United States Patent
Zhebrovska et al.

(10) Patent No.: US 8,404,857 B2
(45) Date of Patent: Mar. 26, 2013

(54) α-CRYSTALLINE FORM OF CARBABENZPYRIDE

(75) Inventors: Filya Zhebrovska, Kiev (UA); Viktor Margitych, Kiev (UA); Grygorii Kostiuk, Kiev (UA); Oleh Syarkevych, Kiev (UA); Mykhailo Vanat, Kiev (UA)

(73) Assignee: Farmak International Holding GmbH, Vienna (AT)

( * ) Notice: Subject to any disclaimer, the term of this patent is extended or adjusted under 35 U.S.C. 154(b) by 0 days.

(21) Appl. No.: 13/576,885

(22) PCT Filed: Jun. 15, 2011

(86) PCT No.: PCT/EP2011/059922
§ 371 (c)(1),
(2), (4) Date: Aug. 2, 2012

(87) PCT Pub. No.: WO2011/157743
PCT Pub. Date: Dec. 22, 2011

(65) Prior Publication Data
US 2012/0309978 A1    Dec. 6, 2012

(30) Foreign Application Priority Data

Jun. 17, 2010  (WO) .................. PCT/IB2010/001956

(51) Int. Cl.
*C07D 213/81*    (2006.01)
(52) U.S. Cl. ..................................... 546/323
(58) Field of Classification Search ......... None
See application file for complete search history.

(56) References Cited

FOREIGN PATENT DOCUMENTS
SU    583612    10/1975

OTHER PUBLICATIONS

N. Nesterova et al., "Studying of Anti-Epstein-Barr Virus Activity of Amizon and their Derivative", Antibiral Research, Elsevier BV, NL, 78(2), p. A61 (Mar. 19, 2008)—XP022541825.
T.A. Bukhtiarova et al., "Structure and Antiinflammatory Activity of Isonicotinic and Nicotinic Amides", Pharmaceutical Chemistry Journal, 31(11), pp. 597-599 (Jan. 1, 1997)—XP002501345.

*Primary Examiner* — Zinna Northington Davis
(74) *Attorney, Agent, or Firm* — Edwards Wildman Palmer LLP; Peter F. Corless; Christine C. O'Day

(57) ABSTRACT

The present invention relates to a new crystalline form of carbabenzpyride of formula (I) and the process for its preparation. Further, the invention relates to the use of this new crystalline form of carbabenzpyride in the treatment and prevention of viral infections.

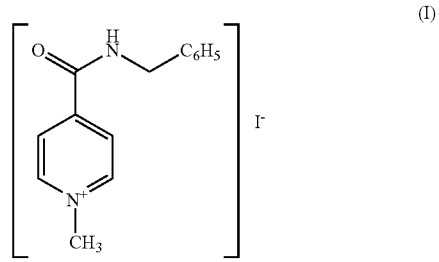

26 Claims, 6 Drawing Sheets

α-CRYSTALLINE FORM OF CARBABENZPYRIDE

CONTINUING DATA

This application is a 371 of PCT/EP2011/059922 filed Jun. 15, 2011.

FIELD OF THE INVENTION

The present invention relates to a new crystalline form of carbabenzpyride and to a method for its preparation. Further, the invention relates to a pharmaceutical composition comprising the new crystalline form, i.e., the α-crystalline form of carbabenzpyride. Finally, the invention relates to the use of the α-crystalline form of carbabenzpyride for the preparation of a medicinal product for the treatment or prevention of viral infections.

Carbabenzpyride has the formula (I):

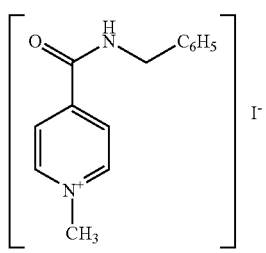

and is also known as Amizon.

BACKGROUND OF THE INVENTION

The pharmaceutically acceptable salts of carbabenzpyride have valuable pharmacologically properties.

Their principal property is the treatment and prevention of viral infections more specifically those caused by influenza A viruses.

For the pharmaceutical use it is of major interest to have a highly pure substance. In addition it is advisable to use a stable, robust and scalable industrial process resulting in a very consistent quality of the product which should be suitable for pharmaceutical formulations.

DESCRIPTION OF THE PRIOR ART

SU 583612 (1975) describes the synthesis of carbabenzpyride as a use for pharmaceutical purposes but there is no sufficient description on obtaining the drug substance in a reproducible manner.

Hence, there was a need for a route of synthesis which provides a highly pure material complying with the requirements for a pharmaceutical use.

SUMMARY OF THE INVENTION

The present invention relates to α-crystalline form of carbabenzpyride of formula (I):

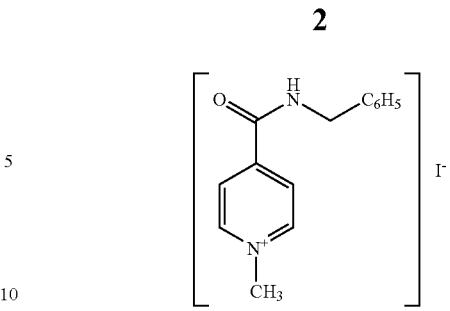

exhibiting essentially the following powder X-ray diffraction data, measured using a diffractometer (copper anticathode) and expressed in terms of inter-planar distance d, Bragg's angle 2 theta, and relative intensity (expressed as a percentage with respect to the most intense ray) as shown in the table below listing the following reflex positions of high and medium intensity:

| No | Angle 2 theta (°) | Inter-planar distance d (Å) | Relative Intensity |
|---|---|---|---|
| 1 | 2.3925 | 36.92687 | 5.23 |
| 2 | 10.2105 | 8.66366 | 5.95 |
| 3 | 11.3179 | 7.81828 | 5.70 |
| 4 | 12.3706 | 7.15527 | 10.86 |
| 5 | 13.9617 | 6.34318 | 3.67 |
| 6 | 16.2837 | 5.44354 | 6.62 |
| 7 | 17.4171 | 5.09177 | 8.45 |
| 8 | 17.6238 | 5.03251 | 66.93 |
| 9 | 19.8858 | 4.46489 | 100.00 |
| 10 | 20.3088 | 4.37284 | 7.36 |

This new α-crystalline form of carbabenzpyride is obtainable by the process according to the present invention comprising the following steps:
(i) condensation of isonicotinic acid with benzylamine at elevated temperatures,
(ii) crystallisation and isolation of the condensation product obtained in step (i) above,
(iii) reaction of the crystalline product obtained in step (ii) above with methyl iodide and
(iv) re-crystallisation of the crude product obtained in step (iii) from aqueous alcohol.

DETAILED DESCRIPTION OF THE INVENTION

According to the process of the present invention a new crystalline form of carbabenzpyride (Amizon) can be obtained which is highly pure. As shown in the experimental section hereinafter, the new crystalline form according to the present invention has a purity of at least 99.5% and preferably of at least 99.9% as determined by HPLC.

Figure 1:
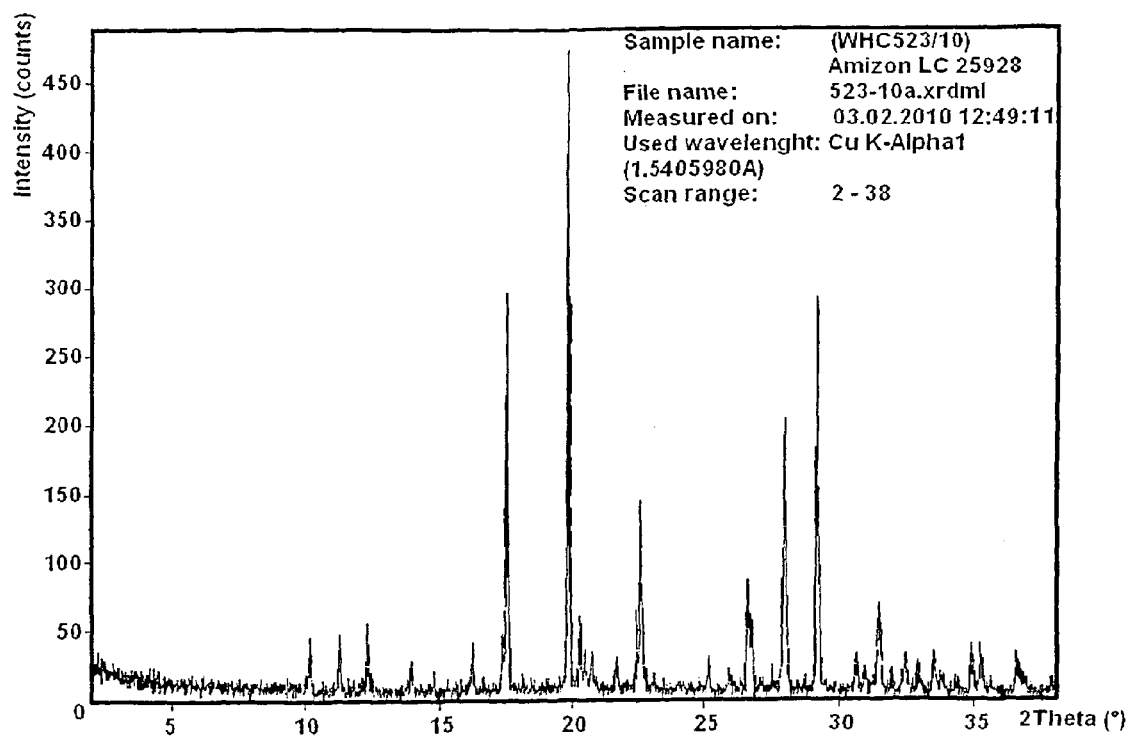
FIG. 1 represents a powder X-ray diffraction diagram of the α-crystalline form of carbabenzpyride according to the present invention.

This new crystalline form of carbabenzpyride, i.e. the α-form, is characterised by its X-ray spectrum as defined in claim 1 listing reflex positions of high and medium intensity. For the sake of completeness, Table 1 below also includes the remaining peaks as shown in the X-ray spectrum according to FIG. 1.

TABLE 1

| No | Angle 2 theta (°) | Inter-planar distance d (Å) | Relative Intensity |
|---|---|---|---|
| 1 | 2.3925 | 36.92687 | 5.23 |
| 2 | 10.2105 | 8.66366 | 5.95 |
| 3 | 11.3179 | 7.81828 | 5.70 |
| 4 | 12.3706 | 7.15527 | 10.86 |
| 5 | 13.9617 | 6.34318 | 3.67 |
| 6 | 16.2837 | 5.44354 | 6.62 |
| 7 | 17.4171 | 5.09177 | 8.45 |
| 8 | 17.6238 | 5.03251 | 66.93 |
| 9 | 19.8858 | 4.46489 | 100.00 |
| 10 | 20.3088 | 4.37284 | 7.36 |
| 11 | 20.5068 | 4.33105 | 5.19 |
| 12 | 20.7785 | 4.27505 | 7.36 |
| 13 | 21.6883 | 4.09772 | 5.43 |
| 14 | 22.4553 | 3.95946 | 4.96 |
| 15 | 22.6282 | 3.92959 | 14.19 |
| 16 | 25.1931 | 3.53505 | 4.53 |
| 17 | 25.9608 | 3.43222 | 3.74 |
| 18 | 26.6025 | 3.35087 | 8.50 |
| 19 | 26.7790 | 3.32918 | 8.32 |
| 20 | 27.5071 | 3.24270 | 1.17 |
| 21 | 27.9630 | 3.19085 | 34.11 |
| 22 | 28.0126 | 3.18531 | 21.03 |
| 23 | 29.1890 | 3.05956 | 42.84 |
| 24 | 30.6379 | 2.91809 | 7.69 |
| 25 | 30.9488 | 2.88949 | 4.47 |
| 26 | 31.4818 | 2.84177 | 11.23 |
| 27 | 31.9139 | 2.80427 | 4.62 |
| 28 | 32.4529 | 2.75892 | 10.21 |
| 29 | 32.8634 | 2.72539 | 5.97 |
| 30 | 33.4828 | 2.67638 | 8.52 |
| 31 | 33.7418 | 2.65642 | 2.46 |
| 32 | 34.3000 | 2.61446 | 1.16 |
| 33 | 34.8705 | 2.57298 | 5.13 |
| 34 | 35.2361 | 2.54712 | 12.94 |
| 35 | 35.5986 | 2.52201 | 1.36 |
| 36 | 36.5494 | 2.45855 | 9.04 |
| 37 | 36.7967 | 2.44260 | 1.16 |
| 38 | 37.7826 | 2.38110 | 1.78 |

Figure 2:
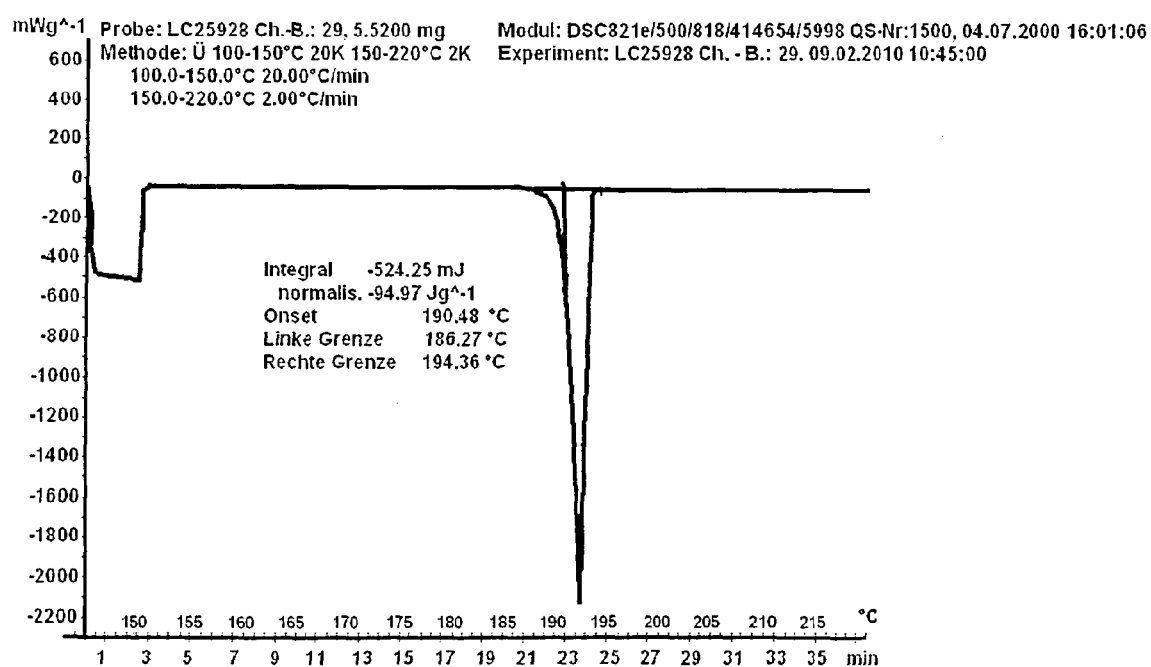
FIG. 2 represents a differential scanning calorimetry curve of the α-form.

The α-form of carbabenzpyride is further characterised by its DSC curve as shown in FIG. 2 (this figure also includes the measuring conditions). The α-crystalline form exhibits an endothermic maximum in its DSC curve in the range of 187 to 199° C. and, in particular, 189.0 to 191.0° C.

Figure 3:
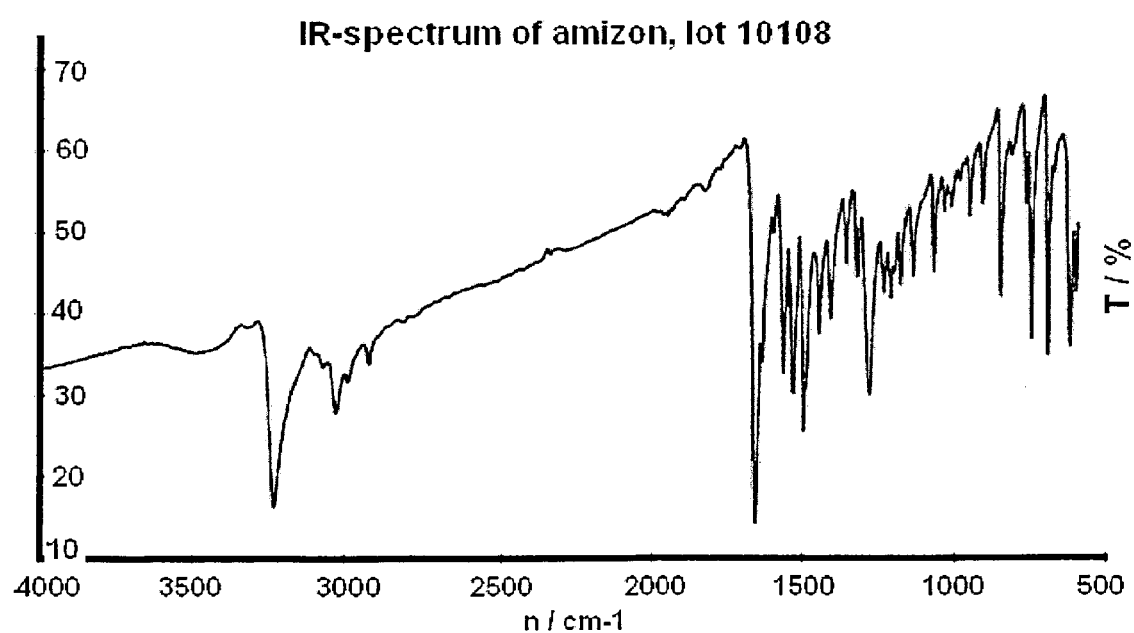
FIG. 3 represents an infrared spectrum of the α-form.
Figure 4:
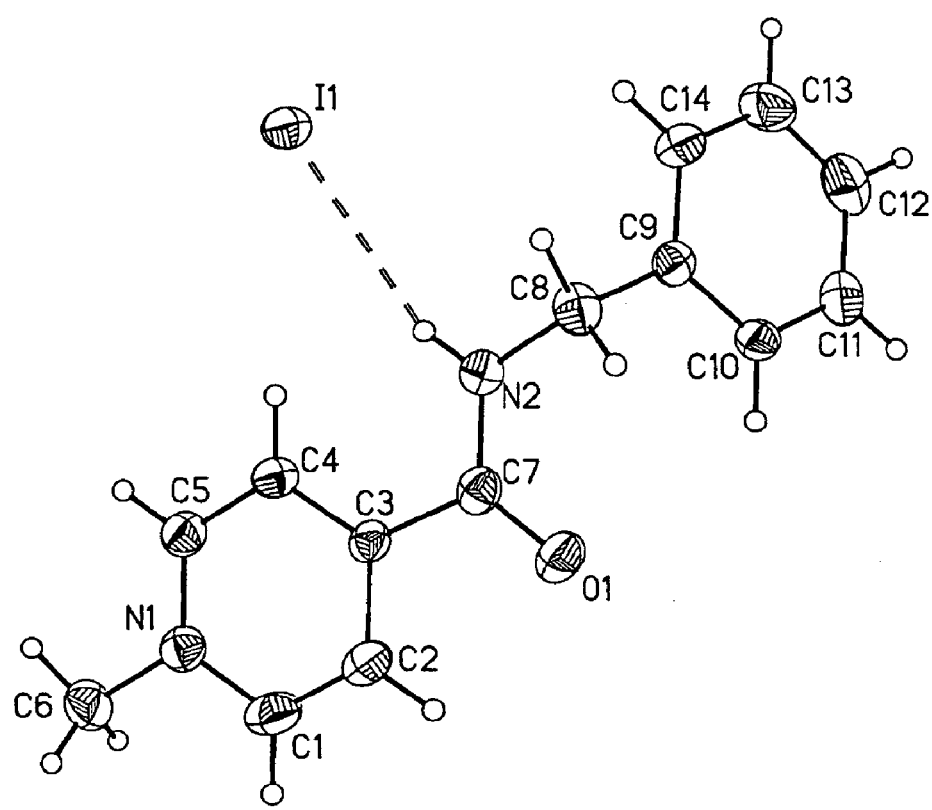
FIG. 4 represents a view of a molecule of carbabenzpyride from the crystal structure showing the numbering scheme employed. Anisotropoic atomic displacement ellipsoids for the non-hydrogen atoms are shown at the 50% probability level. Hydrogen atoms are displaced with an arbitrarily small radius.
Figure 5:
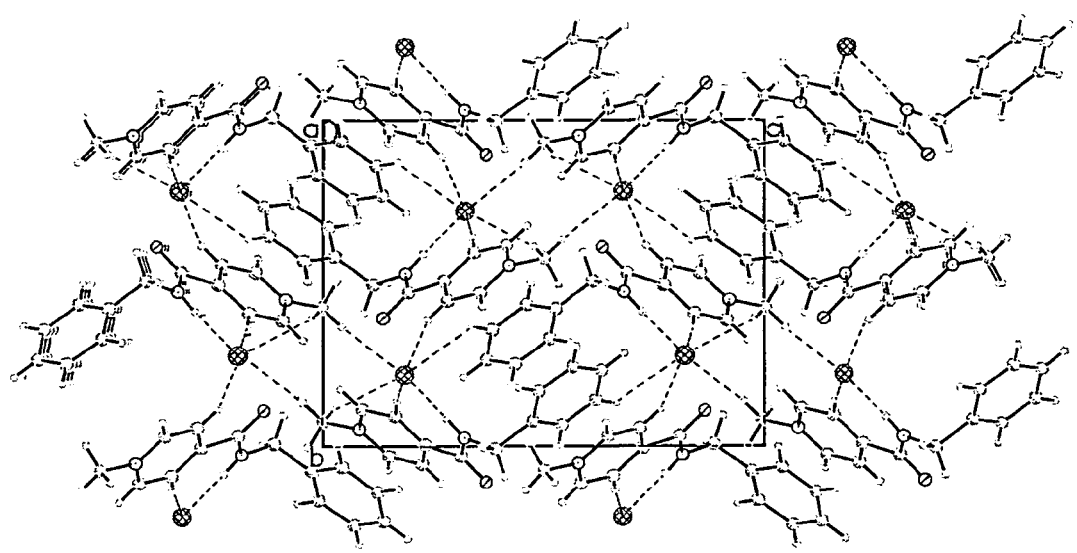
FIG. 5 shows a view of the molecular packing for the α-crystalline form of carbabenzpyride obtained from the crystal structure. (Final cell constants: a=9.27390(10) Å, b=10.7187(2) Å, c=14.2161(2) Å, α=90°, β=90°, γ=90°, volume=1413.14(4) Å$^3$. Final residuals: R1 [for 4152 I>4σ(I)]= 1.87% wR2 [for all 4309 data]=4.40%).
Figure 6:
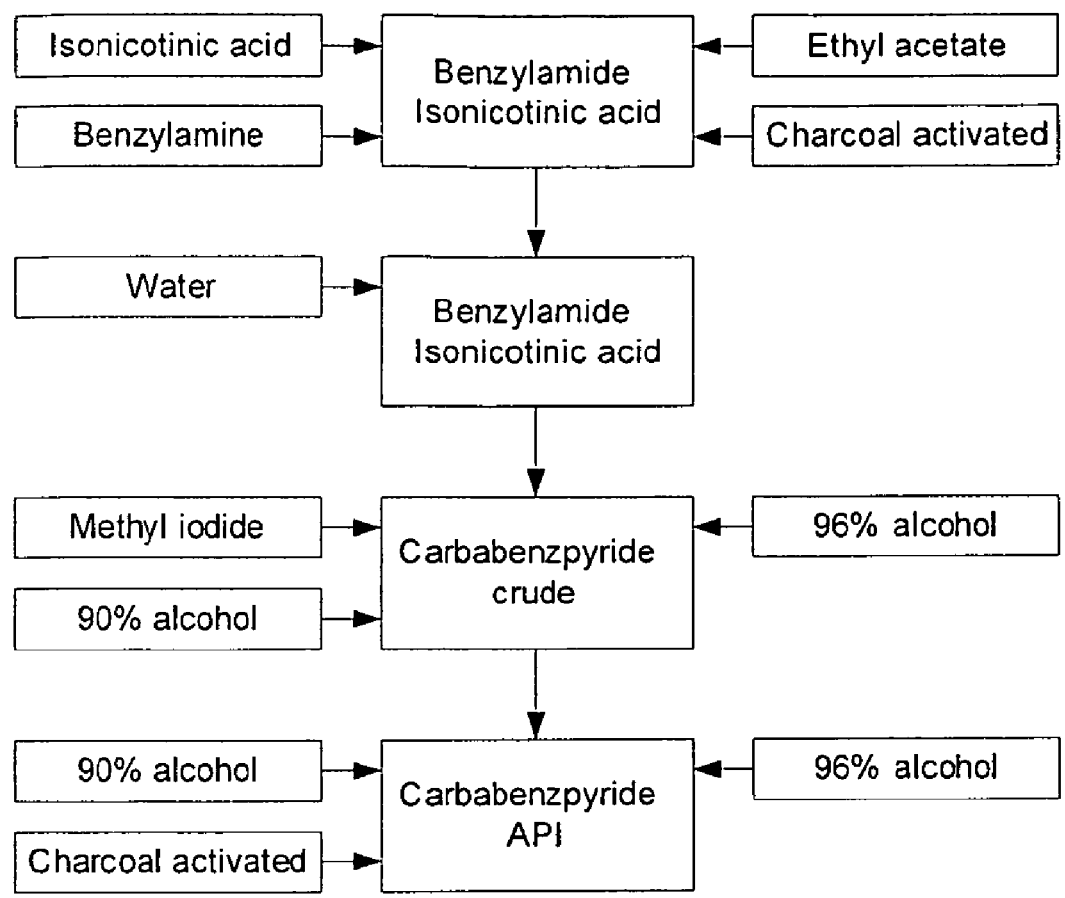
FIG. 6 schematically shows a preferred embodiment of the process for the preparation of the α-crystalline form of carbabenzpyride according to the present invention.

In addition, the α-form of carbabenzpyride is characterised by its IR-spectrum as shown in FIG. 3 exhibiting characteristic peaks listed in the following Table 2.

TABLE 2

| Wave number [cm$^{-1}$] | vibration |
|---|---|
| 3236 | N—H |
| 3040 | C—H |
| 2934 | C—H |
| 1622 | C=O |
| 1600/1502 | C=C |
| 760/704 | C—H |

As mentioned above, the α-crystalline form of carbabenzpyride has a purity of at least 99.5% and preferably of at least 99.9% as determined by HPLC.

Such a high purity could not be achieved in the prior art. In particular, it is possible by using the process according to the present invention to considerably reduce the content of the known genotoxic substance methyl iodide in the final product.

As mentioned above, the process according to the present invention comprises four basic steps, namely (i) condensation of isonicotinic acid with benzylamine at elevated temperatures, (ii) crystallisation and isolation of the condensation product obtained in step (i) above, (iii) reaction of the crystalline product obtained in step (ii) above with methyl iodide and (iv) re-crystallisation of the crude product obtained in step (iii) from aqueous alcohol.

This process is exemplified in the scheme below:

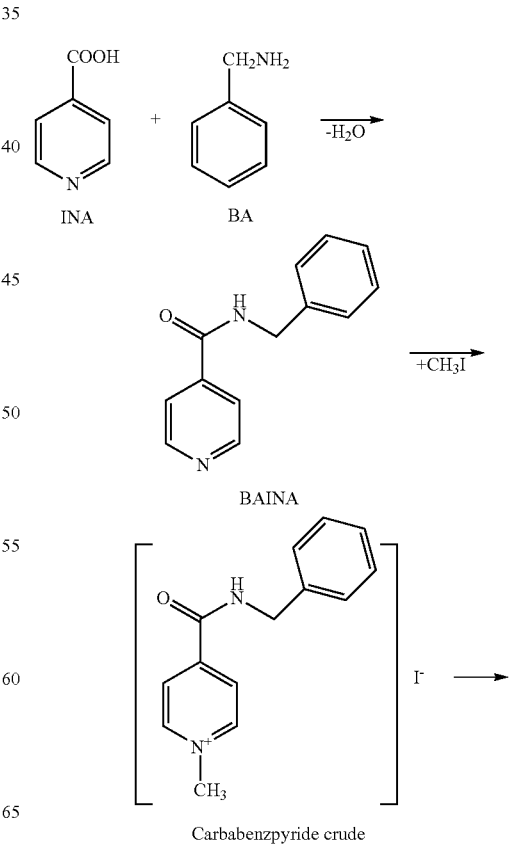

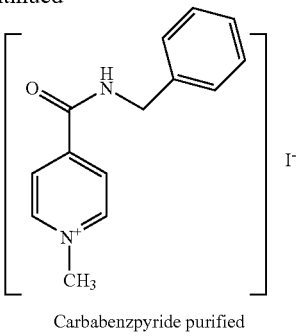

Carbabenzpyride purified wherein INA denotes isonicotinic acid, wherein BA denotes benzylamine and wherein BAINA denotes benzylamide isonicotinic acid.

The condensation of isonicotinic acid with benzylamine is carried out at elevated temperatures, i.e., at temperatures in the range of 160 to 220° C.

The most preferred temperature is in the range of 200 to 210° C.

The mole ratio of isonicotinic acid and benzylamine is in the range of 1:(1.1-1.25).

The most preferred ratio is about 1:1.23.

In the reaction of isonicotinic acid and benzylamine, water is generated which is removed by distillation with benzylamine excess.

The condensation product, namely benzylamide isonicotinic acid (BAINA) is isolated from the reaction mixture by adding a solvent selected from the group consisting of ethyl acetate, acetonitrile and isopropanol.

The most preferred solvent is ethyl acetate.

According to a preferred embodiment of the process according to the present invention the BAINA-solution comprising the above solvent, and preferably ethyl acetate, is treated with activated carbon.

The activated carbon is used in the amount of 0.5% to 1.5% of the volume of solvent, preferably about 1%.

The treating time with activated carbon is 20 to 40 min, preferably about 30 min.

The treating temperature with activated carbon is 65 to 75° C., preferably about 70° C.

Next, the activated carbon or charcoal is filtrated off and the filtrate is spontaneously cooled to a temperature in the range of 25 to 35° C., preferably about 30° C.

Spontaneous cooling means that the solution is simply left standing until it reaches the desired temperature without any additional measures or means been taken to accelerate the cooling process.

After this spontaneous cooling to the aforementioned temperature, a cooling agent is used to lower the temperature to about 0 to 5° C.

Following stirring, the obtained crude product is collected. It is in the form of a paste which is treated with water. The mass ratio of BAINA paste and water is in the range 1:2 to 1:3, preferably about 1:2.

This aqueous system is heated to a temperature in the range of 30 to 40° C., and preferably 32 to 35° C. The stirring time is in the range of 1.5 to 2.5 hours, and preferably about 2 hours.

After filtration, the precipitate is rinsed two times with cold water and subsequently dried, for example, at 25° C. for 18 hours.

The above mentioned process steps result in a BAINA product which is a homogeneous crystalline powder having a yellow to yellow-green colour and a content of impurities of not more than 0.5%.

This high degree of purity makes it possible to accurately calculate the amount of methyl iodide for use in the third step of the process according to the present invention.

Generally, the quaternization reaction of BAINA and methyl iodide is carried out using an excess of methyl iodide in a range of 5 to 15% and preferably 8 to 12%.

The most preferred excess of methyl iodide is about 10%.

According to a preferred embodiment of the process according to the present invention the quaternisation reaction is carried out in an aqueous alcohol solution. The content of water in the alcohol is in general in the range of 5 to 15% and preferably 8 to 12%.

Most preferably the water content is about 10% and the alcohol is ethanol.

The crude product of the quaternisation reaction can be isolated by filtration and is preferably washed with an aqueous alcohol solution. Most preferably 96% ethanol is used.

The pure α-form of carbabenzpyride according to the present invention is obtained by means of re-crystallisation of the crude product obtained in step (iii) from aqueous ethanol.

In general, the amount of water present in the ethanol ranges from 5 to 15% and preferably 7 to 13%.

Most preferably 90% ethanol is used in step (iv).

According to a preferred embodiment of the claimed process the ratio of solvent to crude product used in step (iv) is in the range of 1:2 to 1:4.

The most preferred ratio is about 1:3.

After dissolving the crude product in the solvent, preferably in 90% ethanol, the solution is spontaneously (i.e. without a cooling agent) cooled from the reflux temperature of the solvent to a temperature in the range of 30 to 40° C.

Most preferably the hot solution is cooled spontaneously (i.e. without a cooling agent) to a temperature of about 30° C.

Subsequently, the temperature is further lowered to 10 to 15° C.

After stirring for a period of time in the range of 1 to 3 hours, the pure product can be filtered off and rinsed, for example, two times with cold 96% alcohol.

According to a preferred embodiment of the re-crystallisation process, activated charcoal is added to the solution of the crude product.

The invention also relates to pharmaceutical preparations containing as active ingredient the α-crystalline form of formula (I) together with one or more pharmaceutically acceptable, inert excipients. The formulation may be used as oral, nasal, rectal or parenteral administration in form of tablets, coated tablets, gelatin capsules, lozenges, drinkable solutions, nasal sprays, injectable solutions, suppositories, inhalable solution or powder, etc.

The useful dosage can be varied from 125 mg up to 2500 mg per day either in one or up to 4 individual doses.

The pharmaceutical preparations according to the present invention can be used in the treatment of prevention of viral infections. In particular, they are useful for infections caused by influenza (A) viruses such as, for example, virus strain types A [H3N2 (California and Victoria/3/75), H1N1 (New Caledonia 20/99)].

In addition, the new α-crystalline form of carbabenzpyride according to the present invention and the pharmaceutical compositions comprising this compound show antiviral activity against adenoviruses, coxsackievirus, echovirus, cytomegalovirus, metapneumovirus, and enterovirus as determined by virus yield assay.

Finally, it has been discovered that the new α-crystalline form has an impact on the interferon content in the blood plasma of influenza patients. The effect of the α-crystalline form of carbabenzpyride of formula (I) according to the present invention on cell-mediated immune responses improves clinical course of acute respiratory disease and limits possibilities of development of viral immunosuppression, complications, and transfer of infection into chronic one. Increase of IFN-γ production is of special importance, as, besides antiviral activity, it exerts various effects on immune system cells, myelomonocytic cells, and is deemed a key cytokine accompanying antigen stimulation of lymphocytes.

The following examples illustrate the invention but do not limit it in any way.

Experimental Part

Preparation of BAINA

Example 1

A mixture of 91.4 g (0.7424 M) of isonicotinic acid and 97.9 g (0.9136 M) of benzylamine (1:1.23) is heated to a temperature of 180° C. using a reflux condenser and stirred for 1 h. The temperature of the reaction is reduced to 160° C. herewith. The reaction mass is then heated to a temperature of 210° C. for 2 h using a direct condenser to distil off hydrous benzylamine. The reaction is heated to a temperature of 220° C. for 1.5 h using a direct condenser to distil off excess benzylamine. The content of the reactor is cooled to a temperature of 100° C., and 240 ml of ethyl acetate are added, the reaction is further stirred for 20 min, and 2.4 g of charcoal are added, and the reaction is stirred at a temperature of 70-75° C. for 30 min, filtrated from the charcoal, and the obtained solution is spontaneously cooled to 30° C., then with a cooling agent to 0-+5° C., stirred for 1 h and filtrated.

The BAINA paste is dissolved in 180 ml of water, heated to a temperature of 32-35° C. and stirred for 2 h.

The reaction is filtrated, and the precipitate in the filter is rinsed 2 times in 50 ml of cooled water. The product is dried at 25° C. for 18 h.

Quantity of BAINA: 136.5 g (86.6%).
Analytic Control:
Assay: 101.44%
Content of Related Substances:

| BA, % | INA, % | Any impurity (total), % |
| --- | --- | --- |
| 0.1 | absent | 0.1 |

Example 2

This Example differs from Example 1 in that:
1. A mixture of 294 g (2.39 M) of isonicotinic acid and 316.0 g (2.95 M) of benzylamine is heated.
2. 772 ml of ethyl acetate are added.
3. The BAINA paste is dissolved in 500 ml of water.
Quantity of BAINA: 413.6 g (81.6%).

Example 3

This Example differs from Example 1 in that:
1. A mixture of 45.7 g (0.3715 M) of isonicotinic acid and 49.1 g (0.4589 M) of benzylamine is heated.
2. 120 ml of ethyl acetate are added.
3. The BAINA paste is dissolved in 80 ml of water.
Quantity of BAINA: 65.1 g (82.6%).

Preparation of Crude Carbabenzpyride

Example 4

106.1 g (0.5 M) of BAINA are placed in a reactor fitted with a stirrer, reflux condenser and a dropping funnel, 230 ml of 90% alcohol are added, and the reaction is heated to 38-40° C. and stirred for 30 min upon obtaining a solution. 2.3 g of charcoal are added, and the reaction is heated at a temperature of 60-70° C. for 30 min, after which time the reaction is filtrated and the charcoal on the filter is rinsed 2 times with 5 ml of 90% alcohol. The obtained solution is heated to a temperature of 40-41° C., and 78.1 g (0.55 M) of methyl iodide were added dropwise. The reaction was stirred at a temperature of 40-41° C. for 1 h, heated to boiling and boiled for 1 h. The reaction is spontaneously cooled to a temperature of 40° C., then to a temperature of 10-15° C. in a water bath, and stirred for 1.5 h at this temperature (without seed crystals). The reaction is filtrated and the precipitate is rinsed on the filter 2 times with 55 ml of cooled 96% alcohol.

The product is dried at 25° C. for 18 h and weighed.
Quantity of crude carbabenzpyride: 164.6 g (92.9%)
Analytic Control:
Assay: 102.05%
Content of Related Substances:

| BA, % | BAINA, % | INA, % | Any other impurity, % |
| --- | --- | --- | --- |
| absent | 0.3 | absent | 0.05 |

Example 5

This Example differs from Example 4 in that for the reaction of quaternization 398 g of BAINA (1.88 M), 868 ml of 90% alcohol and 292.0 g (2.06 M) of methyl iodide are used.
Quantity of crude carbabenzpyride paste: 586.8 g

Example 6

This Example differs from Example 4 that for reaction of quaternization 30 g (0.14 M) of BAINA, 63.5 ml of 90% alcohol, 21.42 g (0.15 M) of methyl iodide are used.
Quantity of crude carbabenzpyride paste: 42.9 g Preparation of the Pure α-Crystalline Form of Carbabenzpyride

Example 7

580 g of crude carbabenzpyride are dissolved in 1744 ml of 90% alcohol (1:3) (m/V), and 17 g of activated charcoal are added. The reaction is heated to boiling temperature, stirred at boiling for 30 min and filtrated. The obtained solution is spontaneously cooled to a temperature of 30° C., then to a temperature of 10-15° C. in a cooling water bath, then stirred for 1 h at this temperature (without seed crystals), filtrated to obtain a solution and the filter is rinsed 2 times with 105 ml of cooled 96% alcohol.

The product is dried at 25° C. for 18 h and weighed.
Quantity of purified carbabenzpyride: 502.8 g (62.5% based on isonicotinic acid).
Analytic Control:
Assay: 100.97%
Content of Related Substances:

| BA, % | BAINA, % | Total impurity, % |
| --- | --- | --- |
| absent | 0.01 | 0.01 |

Example 8

This Example differs from Example 7 in that for the re-crystallisation reaction 30 g of crude carbabenzpyride, 90 ml of 90% alcohol, and 0.1 g of activated charcoal are used.

Quantity of purified carbenzpyride: 25.6 g (60.3% based on isonicotinic acid).
Analytic Control:
Assay: 100.58%
Content of Related Substances:

| BA, % | BAINA, % | Total impurity, % |
|---|---|---|
| 0.005 | absent | 0.005 |

Example 9

This Example differs from Example 7 in that for the re-crystallisation, 500 g of carbabenzpyride crude, 1500 ml of 90% alcohol, 15 g of activated charcoal is used.

Quantity of purified carbabenzpyride: 425.79 g (75.4% based on isonicotinic acid).
Analytic Control:
Assay: 99.48%
Content of Related Substances:

| BA, % | BAINA, % | Total impurity, % |
|---|---|---|
| 0.01 | 0.015 | 0.03 |

Example 10

50 g of crude carbabenzpyride are dissolved in 150 ml of 90% alcohol (1:3) (m/V), 1.5 g of activated charcoal are added and the reaction is heated to boiling temperature, stirred at boiling for 30 min and filtrated. The obtained solution is spontaneously cooled to a temperature of 30° C., then to a temperature of 10-15° C. in a cooling water bath, stirred for 1 h at this temperature (without seed crystals), filtrated to obtain a solution and the filter is rinsed 2 times with 20 ml of cooled 96% alcohol.

The product is dried at 25° C. for 18 h and weighed.
Quantity of purified carbabenzpyride: 44 g (70.8% based on isonicotinic acid).
Analytic Control:
Melting point: 191.3° C.
Assay: 99.81%
Content of Related Substances:

| BA, % | BAINA, % | Total impurity, % |
|---|---|---|
| absent | 0.01 | 0.03 |

Example 11

This Example differs from Example 10 in that 70% alcohol is used as solvent.

Quantity of purified carbabenzpyride: 33 g (53.1% based on isonicotinic acid).
Analytic Control:
Melting point: 191.5° C.
Assay: 101.01%
Content of Related Substances:

| BA, % | BAINA, % | Total impurity, % |
|---|---|---|
| absent | 0.03 | 0.05 |

Example 12

This Example differs from Example 10 in that water is used as the solvent.

Quantity of purified carbabenzpyride: 40.6 g (65.4% based on isonicotinic acid).
Analytic Control:
Melting point: 191.4° C.
Assay: 100.19%
Content of Related Substances:

| BA, % | BAINA, % | Total impurity, % |
|---|---|---|
| absent | 0.14 | 0.2 |

Example 13

This Example differs from Example 10 in that crude carbabenzpyride was purified, and carbabenzpyride was subjected to a second re-crystallisation using water as solvent. 40 g of purified carbabenzpyride are dissolved in 460 ml of water at a temperature of 30-35° C., stirred for 20 min, and then spontaneously cooled to a temperature of 22-25° C., further stirred for 1 h, then cooled for 2 h to a temperature of 7-10° C. and filtrated.

Quantity of purified carbabenzpyride: 29.5 g (73.8%, based on purified carbabenzpyride)
Analytic Control:
Melting point: 191.1° C.
Assay: 99.11%
Content of Related Substances:

| BA, % | BAINA, % | Total impurity, % |
|---|---|---|
| absent | 0.007 | 0.04 |

Crystal Structure Information (α-Crystalline Form of Carbabenzpyride)

A yellow prism of $C_{14}H_{15}IN_2O$, approximate dimensions 0.26 mm×0.34 mm×0.40 mm, was used for the X-ray crystallographic analysis. The X-ray intensity data were measured at 173(2) K on a Bruker SMART APEX II system equipped with a graphite monochromator and a MoKα fine-focus sealed tube (λ=0.71073 Å) operated at 1250 W power (50 kV, 25 mA). The detector was placed at a distance of 60 mm from the crystal. 458 frames were collected with a scan width of 1.5° in ω and an additional 211 frames were collected with a scan width of 1.5° in φ. All frames were collected with an exposure time of 20 sec/frame. The total data collection time was 5 hours. The frames were integrated with the Bruker SAINT software package using a narrow-frame integration algorithm. The integration of the data using a Orthorhombic cell yielded a total of 18403 reflections to a maximum θ angle of 30.54° (0.7 Å resolution), of which 4309 were independent (redundancy 4.27, completeness=99.7%, $R_{int}$=2.67%, $R_{sig}$=2.29%) and 4152 (96.4%) were greater than 4σ($F^2$). The final cell constants of a=9.27390(10) Å, b=10.7187(2) Å, c=14.2161(2) Å, α=90°, β=90°, γ=90°, volume=1413.14(4) Å$^3$, are based upon the refinement of the XYZ-centroids of 9894 reflections above 20σ(I) with 2.38°<2θ<30.54°. Analysis of the data showed negligible decay during data collection. Data were corrected for absorption effects using the numerical technique (SADABS). The ratio of minimum to maximum apparent transmission was 0.79. The calculated minimum and maximum transmission coefficients (based on crystal size) are 0.4625 and 0.5872.

The structure was solved and refined using the Bruker SHELXTL (Version 6.1) Software Package, using the space group P2(1)2(1)2(1), with Z=4 for the formula unit, $C_{14}H_{15}IN_2O$. The final anisotropic full-matrix least-squares refinement on $F^2$ with 164 variables converged at R1=1.87%, for the observed data and wR2=4.40% for all data. The goodness-of-fit was 1.117. The largest peak on the final difference electron density synthesis was 0.260 e$^-$/Å$^3$ and the largest hole was −0.752 e$^-$/Å$^3$ with an RMS deviation of 0.093 e$^-$/Å$^3$. On the basis of the final model, the calculated density was 1.665 g/cm$^3$ and F(000), 696 e$^-$.

The results of the X-ray crystal graphic analysis is summarised in the following tables below:

TABLE 3

Sample and crystal data

| | |
|---|---|
| Identification code | BatchNo38 |
| Compound Name | BatchNo38 |
| Empirical formula | C14 H15 I N2 O |
| Molecular formula | C14 H15 I N2 O |
| Formula weight | 354.18 |
| Temperature | 173(2) K |
| Wavelength | 0.71073 Å |
| Crystal size | 0.40 × 0.34 × 0.26 mm |
| Crystal habit | yellow prism |
| Crystal system | Orthorhombic |
| Space group | P2(1)2(1)2(1) |
| Unit cell dimensions | a = 9.27390(10) Å    α = 90° |
| | b = 10.7187(2) Å     β = 90° |
| | c = 14.2161(2) Å     γ = 90° |
| Volume | 1413.14(4) Å$^3$ |
| Z | 4 |
| Density (calculated) | 1.665 Mg/m$^3$ |
| Absorption coefficient | 2.257 mm$^{-1}$ |
| F(000) | 696 |

TABLE 4

Atomic coordinates and equivalent isotropic atomic displacement parameters (Å$^2$).

| | x/a | y/b | z/c | U(eq) |
|---|---|---|---|---|
| I1 | 0.059362(13) | 0.220079(11) | 0.681751(8) | 0.02914(4) |
| N1 | 0.69454(18) | 0.05287(15) | 0.58001(10) | 0.0271(3) |
| N2 | 0.28947(17) | 0.02738(14) | 0.81732(11) | 0.0264(3) |
| O1 | 0.46021(17) | −0.10841(13) | 0.86668(9) | 0.0349(3) |
| C1 | 0.7327(2) | −0.0307(2) | 0.64696(15) | 0.0364(5) |
| C2 | 0.6437(2) | −0.0549(2) | 0.72023(15) | 0.0345(4) |
| C3 | 0.5104(2) | 0.00550(17) | 0.72769(12) | 0.0237(3) |
| C4 | 0.4756(2) | 0.09259(18) | 0.65976(12) | 0.0264(4) |
| C5 | 0.5688(2) | 0.11448(17) | 0.58631(12) | 0.0276(4) |
| C6 | 0.7919(2) | 0.0751(2) | 0.49994(13) | 0.0373(5) |

TABLE 4-continued

Atomic coordinates and equivalent isotropic atomic displacement parameters (Å$^2$).

| | x/a | y/b | z/c | U(eq) |
|---|---|---|---|---|
| C7 | 0.4168(2) | −0.02994(16) | 0.81034(12) | 0.0255(4) |
| C8 | 0.1835(2) | −0.00506(18) | 0.88881(12) | 0.0297(4) |
| C9 | 0.1874(2) | 0.07944(16) | 0.97341(12) | 0.0238(3) |
| C10 | 0.2960(2) | 0.06614(17) | 1.04050(13) | 0.0264(4) |
| C11 | 0.2997(2) | 0.1429(2) | 1.11906(13) | 0.0326(4) |
| C12 | 0.1953(3) | 0.2329(2) | 1.13172(14) | 0.0395(5) |
| C13 | 0.0859(3) | 0.2455(2) | 1.06617(16) | 0.0429(5) |
| C14 | 0.0835(2) | 0.1694(2) | 0.98697(14) | 0.0355(4) |

U(eq) is defined as one third of the trace of the orthogonalized $U_{ij}$ tensor.

TABLE 5

Bond lengths (Å)

| | | | |
|---|---|---|---|
| N1—C5 | 1.343(2) | N1—C1 | 1.354(2) |
| N1—C6 | 1.472(2) | N2—C7 | 1.335(2) |
| N2—C8 | 1.456(2) | N2—H2N | 0.8800 |
| O1—C7 | 1.229(2) | C1—C2 | 1.354(3) |
| C1—H1 | 0.9500 | C2—C3 | 1.400(3) |
| C2—H2 | 0.9500 | C3—C4 | 1.381(2) |
| C3—C7 | 1.509(3) | C4—C5 | 1.376(3) |
| C4—H4 | 0.9500 | C5—H5 | 0.9500 |
| C6—H6A | 0.9800 | C6—H6B | 0.9800 |
| C6—H6C | 0.9800 | C8—C9 | 1.506(2) |
| C8—H8A | 0.9900 | C8—H8B | 0.9900 |
| C9—C14 | 1.377(3) | C9—C10 | 1.394(3) |
| C10—C11 | 1.388(3) | C10—H10 | 0.9500 |
| C11—C12 | 1.378(3) | C11—H11 | 0.9500 |
| C12—C13 | 1.385(3) | C12—H12 | 0.9500 |
| C13—C14 | 1.391(3) | C13—H13 | 0.9500 |
| C14—H14 | 0.9500 | | |

TABLE 6

Bond angles (°)

| | | | |
|---|---|---|---|
| C5—N1—C1 | 120.36(17) | C5—N1—C6 | 120.29(16) |
| C1—N1—C6 | 119.35(17) | C7—N2—C8 | 122.64(16) |
| C7—N2—H2N | 118.7 | C8—N2—H2N | 118.7 |
| C2—C1—N1 | 120.51(19) | C2—C1—H1 | 119.7 |
| N1—C1—H1 | 119.7 | C1—C2—C3 | 120.56(18) |
| C1—C2—H2 | 119.7 | C3—C2—H2 | 119.7 |
| C4—C3—C2 | 117.77(18) | C4—C3—C7 | 125.45(17) |
| C2—C3—C7 | 116.78(16) | C5—C4—C3 | 119.93(17) |
| C5—C4—H4 | 120.0 | C3—C4—H4 | 120.0 |
| N1—C5—C4 | 120.82(16) | N1—C5—H5 | 119.6 |
| C4—C5—H5 | 119.6 | N1—C6—H6A | 109.5 |
| N1—C6—H6B | 109.5 | H6A-C6—H6B | 109.5 |
| N1—C6—H6C | 109.5 | H6A-C6—H6C | 109.5 |
| H6B—C6—H6C | 109.5 | O1—C7—N2 | 123.79(18) |
| O1—C7—C3 | 119.43(17) | N2—C7—C3 | 116.79(16) |
| N2—C8—C9 | 113.40(15) | N2—C8—H8A | 108.9 |
| C9—C8—H8A | 108.9 | N2—C8—H8B | 108.9 |
| C9—C8—H8B | 108.9 | H8A-C8—H8B | 107.7 |
| C14—C9—C10 | 118.77(17) | C14—C9—C8 | 121.04(17) |
| C10—C9—C8 | 120.18(17) | C11—C10—C9 | 120.54(18) |
| C11—C10—H10 | 119.7 | C9—C10—H10 | 119.7 |
| C12—C11—C10 | 120.17(19) | C12—C11—H11 | 119.9 |
| C10—C11—H11 | 119.9 | C11—C12—C13 | 119.71(19) |
| C11—C12—H12 | 120.1 | C13—C12—H12 | 120.1 |
| C12—C13—C14 | 119.9(2) | C12—C13—H13 | 120.0 |
| C14—C13—H13 | 120.0 | C9—C14—C13 | 120.87(19) |
| C9—C14—H14 | 119.6 | C13—C14—H14 | 119.6 |

TABLE 7

| Torsion angles (°) | | | |
|---|---|---|---|
| C5—N1—C1—C2 | 1.1(3) | C6—N1—C1—C2 | −178.5(2) |
| N1—C1—C2—C3 | 0.4(3) | C1—C2—C3—C4 | −2.0(3) |
| C1—C2—C3—C7 | 178.4(2) | C2—C3—C4—C5 | 2.0(3) |
| C7—C3—C4—C5 | −178.38(17) | C1—N1—C5—C4 | −1.0(3) |
| C6—N1—C5—C4 | 178.63(18) | C3—C4—C5—N1 | −0.6(3) |
| C8—N2—C7—O1 | −5.2(3) | C8—N2—C7—C3 | 174.76(15) |
| C4—C3—C7—O1 | −179.47(19) | C2—C3—C7—O1 | 0.1(2) |
| C4—C3—C7—N2 | 0.6(3) | C2—C3—C7—N2 | −179.81(18) |
| C7—N2—C8—C9 | 97.4(2) | N2—C8—C9—C14 | 104.6(2) |
| N2—C8—C9—C10 | −76.5(2) | C14—C9—C10—C11 | −0.5(3) |
| C8—C9—C10—C11 | −179.44(17) | C9—C10—C11—C12 | 0.3(3) |
| C10—C11—C12—C13 | 0.6(3) | C11—C12—C13—C14 | −1.4(3) |
| C10—C9—C14—C13 | −0.2(3) | C8—C9—C14—C13 | 178.67(19) |
| C12—C13—C14—C9 | 1.2(3) | | |

Antiviral Activity Against Influenza of the Virus Strain Types A [H3N2 (California and Victoria/3/75), H1N1 (New Caledonia 20/99)]

The purpose of the study described below was to test the antiviral activity of the α-crystalline form of carbabenzpyride having the code name "FAV00A" against different strains of influenza viruses A.

The inhibition of viral infection of cultured MDCK (NBL-2) cells was examined by determining the reduction in virus titres using Virus Yield Reduction Assay. A reference substance (Zanamivir—a neuraminidaseinhibitor) with known antiviral effect against influenza viruses was used as control in monitoring the effectiveness of FAV00A.

1. Materials and Methods

Test System

Cells: Madin-Darby canine kidney cell line MDCK (NBL-2) was obtained from the American Type Culture Collection (ATCC), Rockville, Md., ATCC-number CCL-34. Cell stock was stored in liquid nitrogen. Working stock of NBL-2 were cultured in minimal essential medium (MEM) supplemented with 5% fetal calf serum (FCS) for a maximum of 20 passages according to standard operating procedures (SOP). NBL-2 cells were cultured in 25 cm$^2$ cell culture flasks in MEM at 37° C. and passaged in a dilution of 1:10 or 1:20 twice weekly. For culture in 96 well plates 100 μl cell suspension containing $8*10^4$ cells was dispensed into each well.

Cells were routinely tested fro Mycoplasma by the Venor®GeM Mycoplasma Detection Kit for conventional polymerase chain reaction (Minerva Biolabs GmbH, Berlin, Germany) according to SOP. Cells used for project were free of contamination.

Viruses: Influenza viruses used for the anti-viral testing include Influenza A H1N1 (strain New Caledonia 20/99), Influenza A H3N2 (strains Victoria/3/75 and California), Influenza B (strains Taiwan 2/62 and Jiangsu). Virus stock was prepared by propagating Influenza viruses in serum-free MEM supplemented with 2 μg/ml trypsin using NBL-2 cells as host. After 2-3 days incubation at 37° C., 1% bovine serum albumin (BSA) was added to virus-infected NBL-2 cell culture to ensure stability of virus, before freezing overnight at −80° C. Stock solutions of the virus were prepared from clarified cell culture supernatants by low speed centrifugation and then aliquoted in 500 μl stock. Virus stock was stored at −80° C. until use. The respective infectious virus titres in stock solutions were determined by titration on NBL-2 cell monolayer in 96-well plates and evaluated as 50% tissue culture infective dose ($TCID_{50}$). The infectous titre was determined by the method of Spearman and Kaerber (Spearman C (1908). The method of "right and wrong cases" ("constantstimuli") without Gauss's formulae. British Journal of Psychology 2: 227-242; Kärber G (1931). Beitrag zur kollektiven Behandlung pharmakologischer Reihenversuche [A contribution to the collective treatment of a pharmacological experimental series]. Archiv für experimentelle Pathologie und Pharmakologie 162: 480-483.)

Cell Culture Medium:
MEM, Cat. no. T 031-10, Biochrom
FCS, Cat. no. F-7524, Sigma
Phosphate Buffered Saline (PBS) 10×:
Phosphate buffered saline Cat. no. L 182-10, Dulbecco Biochrom add to 1 l aqua ad injectabila, Cat no. 0370-3452, Braun.
Autoclaved and stored at room temperature, storage life one year; two months in use.
PBS 1×:
450 ml aqua ad injectabila+50 ml 10×PBS
Stored at room temperature, storage life one year; two months in use.
$NaHCO_3$, 7.5%:
75 g $NaHCO_3$, Cat. no. S-4019, Sigma
Dissolve in 1 l Millipore-$H_2O$.
Stored at 2-8° C., storage life one year; two months in use.
Hepes, 1 M:
238.31 g Hepes, Cat no. S-4019, Sigma
33.75 ml NaOH 32%
Dissolve in 1 l Millipore-$H_2O$.
Stored at 2-8° C., storage life one year; four months in use.
L-glutamine, 0.2 M:
29.2 g L-glutamine, Cat. no. G-5763, Sigma
Dissolve in 1 l Millipore-$H_2O$.
Stored at ≦−18° C. for one year; two months at 2-8° C. in use.
Penicillin/Streptomycin:
10 MEGA Penicillin (penicillin), Grünenthal
10 g Streptomycin-Sulfate, Cat no. S-6501, Sigma
Dissolve in 1 l Millipore-$H_2O$.
Stored at ≦−18° C. for one year; two weeks at 2-8° C. in use.
Trypsin/EDTA Solution:
2.0 g Trypsin 1:250 BAEE 1570 units/ml, Cat. no. T-4799, Sigma
0.6 g EDTA-Na (Tritriplex III), Cat. no. 8418.0100, Merck
Dissolve in 1 l 1×PBS.
Stored at ≦−18° C. for one year; one month at 2-8° C. in use.
Serum-free MEM supplemented with 2% hepes, 2% $NaHCO_3$, 1% penicillin/streptomycin and containing 2 μg/ml trypsin was used as maintenance medium.

2. Determination of Antiviral Activity (Virus Yield Reduction Assay)

The virus yield reduction assay is a powerful technique for evaluating the efficacy of anti-viral compounds. This assay allows one to quantitate the production of infectious virions in drug-treated cultures in comparison to virus yields in untreated virus control. In this procedure virus-infected cultures are incubated with anti-viral compounds for a period sufficient to permit virus replication and then assayed for the presence of new progeny virus by titration on separate monolayer cultures (Shipman C Jr, Smith S H, Carlson R H, Drach J C (1976). Antiviral activity of arabinosyladenine and arabinosylhypoxanthine in herpes simplex virus-infected KB cells: selective inhibition of viral deoxyribonucleic acid synthesis in synchronized suspension cultures. Antimicrob Agents Chemother. 9: 120-127; Collins P, Bauer D J (1977). Relative potencies of anti-herpes compounds. Ann N Y Acad Sci. 284: 49-59; Prichard M N, Turk S R, Coleman L A, Engelhardt S L, Shipman C Jr, Drach J C (1990). A microtiter virus yield reduction assay for the evaluation of antiviral compounds against human cytomegalovirus and herpes simplex virus. J Virol Methods. 28: 101-106).

2.1 Assay Principle:

The assay was performed in cell culture flasks in triplicates. Two independent experiments were performed. The concentrations of the test or reference substance used were pre-determined in the cytotoxicity measurements as described above. The highest concentration used should not show any toxic effect on the cells. A preliminary experiment was first carried out in two different variations using 400 µg FAV00A test substance and 10 ng Zanamivir reference substance. The experiment was performed using Influenza B strain Taiwan 2/62 and Influenza A strain New Caledonia. In one variation of the assay, NBL-2 cells were cultured in 25 cm$^2$ cell culture flasks in MEM at 37° C. in a dilution of 1:10. Cells were counted and then infected after washing with PBS at a multiplicity of infection (MOI) of 0.01 for both influenza viruses. To one set (triplicate) of infected cells, 400 µg FAV00A was simultaneously added (at the same time as virus) to the cell culture. The cells were incubated for 45 minutes at 37° C. to allow virus adsorption and then washed thrice with PBS to eliminate unadsorbed viruses. Afterwards, the set of infected cells that was pre-incubated with 400 µg FAV00A was again treated with 400 µg FAV00A. A second set of infected cells was treated with 10 ng Zanamivir. Virus control without addition of test or reference substance was also included in the assay. The second variation of the assay was performed just like the first but without the pre-incubation step with 400 µg FAV00A (simultaneous addition of FAV00A). Here, the cells were first infected with the viruses followed by 45 minutes incubation to allow for virus adsorption. After 3× washing with PBS the infected cell cultures were then treated with 400 µg FAV00A or 10 ng Zanamivir. The culture flasks were incubated at 37° C. in a 5% CO$_2$-incubator for 24 hours and then frozen overnight and thawed the next day. The freezing and thawing steps allow the cells to disintegrate and release the virus they contain. In this way, the total amount of virus can be recovered. After a "low speed" centrifugation the viral amounts in each experimental setup (virus control as well as test or reference substance) is determined by performing an "end point titration" in 96-well plate—this gives the virus titre/amount at which 50% of cells are infected or uninfected (TCID$_{50}$/ml).

All further experiments with all influenza viruses tested were performed using the second variation. For this purpose, cells were counted and then infected after washing with PBS at a multiplicity of infection (MOI) of 0.01 for all influenza viruses used except for H3N2 (California), which was used to infect cells at MOI 0.001. Two different concentrations were tested (400 µg and 800 µg for FAV00A; 100 ng and 1000 ng for Zanamivir).

End Point Titration

One 96-well plate (for each experimental setup) with the susceptible cell culture was prepared according to SOP. Fifty µl of cell suspension was cultured in each well. Cells were cultured at 37° C. and in a 5% CO$_2$ atmosphere for three or four days to form a confluent monolayer. A 10-fold serial dilution (up to $10^{-9}$) of the recovered viruses following low speed centrifugation was made using the maintenance medium. On each plate, the $1^{st}$ and $2^{nd}$ rows (8 wells each) were used for cell culture control, $3^{rd}$-$12^{th}$ rows (8 wells each) were used for 10-fold serially diluted virus, beginning with undiluted virus stock and ending with the $10^{-9}$ diluted virus. Fifty µl from virus dilution was introduced into appropriate rows while 50 µl maintenance medium was added to the cell control rows. The plates were incubated for 2-3 days at 37° C. in a CO$_2$ incubator. After the incubation period, the plates were examined microscopically for cytopathogenic effect (CPE). The examination was performed independently, by two laboratory technicians. The virus titre was then calculated according to the method of Spearman and Kaerber. The % titre reduction in the test or reference substance in comparison to virus control (set to 100%) was then calculated.

2.2 Data Presentation

Virus yield reduction was expressed as TCID$_{50}$/ml and the % of virus infection as well as the fold reduction observed after treatment with test or reference substance relative to virus control (set to 100%) is indicated. As two independent experiments were conducted with the test and reference substances, mean values are presented in the tables below:

TABLE 8

Influenza A strain New Caledonia (H1N1)

| | Titer (TCID$_{50}$/ml) | % virus yield relative to control | Fold reduction |
|---|---|---|---|
| Virus control | 2.11 * 10$^6$ | 100 | — |
| FAV00A 400 µg (with 45 minutes pre-incubation) | 1.10 * 10$^6$ | 52 | 1.92 |
| FAV00A 400 µg (without pre-incubation) | 6.56 * 10$^5$ | 31 | 3.23 |
| Zanamivir 10 ng | 4.85 * 10$^5$ | 23 | 4.35 |

TABLE 9

Influenza A strain California (H3N2)

| | Titer (TCFD$_{50}$/ml) | % virus yield relative to control | Fold reduction |
|---|---|---|---|
| Virus control | 2.95 * 10$^4$ | 100 | — |
| FAV00A 400 µg | 2.25 * 10$^4$ | 76 | 1.32 |
| FAV00A 800 µg | 1.80 * 10$^4$ | 61 | 1.64 |
| Zanamivir 100 ng | 1.18 * 10$^2$ | 0.4 | 250 |

TABLE 10

Influenza A strain Victoria (H3N2)

| | Titer (TCID$_{50}$/ml) | % virus yield relative to control | Fold reduction |
|---|---|---|---|
| Virus control | 2.90 * 10$^6$ | 100 | — |
| FAV00A 400 µg | 1.20 * 10$^6$ | 41 | 2.44 |
| FAV00A 800 µg | 7.75 * 10$^5$ | 27 | 3.70 |
| Zanamivir 100 ng | 7.05 * 10$^2$ | 0.02 | 5000 |

TABLE 11a

Influenza A strain New Caledonia (H1N1)

| | Titer (TCID$_{50}$/ml) | % virus yield relative to control | Fold reduction |
|---|---|---|---|
| Virus control | 2.11 * 10$^6$ | 100 | — |
| FAV00A 400 µg | 6.81 * 10$^3$ | 32 | 3.13 |
| Zanamivir 100 ng | 7.00 * 10$^4$ | 3 | 33.33 |

TABLE 12b

Influenza A strain New Caledonia (H1N1)

| | Titer (TCID$_{50}$/ml) | % virus yield relative to control | Fold reduction |
|---|---|---|---|
| Virus control | 9.70 * 10$^6$ | 100 | — |
| FAV00A 800 µg | 2.70 * 10$^6$ | 28 | 3.57 |
| Zanamivir 100 ng | 1.42 * 10$^6$ | 15 | 6.67 |

3. Conclusion

The above data confirm that FAV00A has antiviral effects against influenza A viruses tested by reducing total virus yield in cultured NBL-2 cells. The time of addition experiments suggest that FAV00A influences steps of the virus adsorption to its specific receptor on the cell surface. These steps include virus uncoating and replication.

Antiviral Activity Against Adenoviruses, Coxsackievirus, Echovirus, Cytomegalovirus, Metapneumovirus, and Enterovirus as Determined by Virus Yield Assay The purpose of this study was to test the influence of the test substance, FAV00A, on the replication of adenoviruses, human metapneumovirus, echo viruses, coxsackie virus A9, enterovirus 71, and human cytomegalovirus as determined by virus titres. Virus titres were determined by Virus Yield Reduction Assay.

1. Materials and Methods 1.1 Study Materials and Preparations
1.1.1 Study Design 1.1.2 Test System
Cells: Human foreskin fibroblasts (HFF) were used to cultivate cytomegalovirus, enterovirus, echo virus, and coxsackievirus A9. HFFs established as described previously [1]. LLC-MK2 (MK2) cells were obtained from the American Type Culture Collection (ATCC, Rockville, Md.) and used for cultivation of metapneumovirus. A549 cells were obtained from ATCC and used for cultivation of adenovirus.

Working stocks of cells were cultured in minimal essential medium (MEM) supplemented with 5% fetal calf serum (FCS) for a maximum of 20 passages. Cells were cultured in 25 cm$^2$ cell culture flasks in MEM at 37° C. For culture in 96 well plates 100 µl cell suspension was dispensed into each well and cells were grown to confluency.

Cells were routinely tested for Mycoplasma by the Venor®GeM Mycoplasma Detection Kit for conventional polymerase chain reaction (Minerva Biolabs GmbH, Berlin, Germany). Cells used for project were free of contamination.

Cell Culture Medium:
MEM, Cat. no. T 031-10, Biochrom
FCS, Cat. no. F-7524, Sigma
Phosphate Buffered Saline (PBS) 10×:
Phosphate buffered saline Cat no. L 182-10, Dulbecco Biochrom add to 1 l aqua ad injectabila, Cat no. 0370-3452, Braun.
Autoclaved and stored at room temperature, storage life one year; two months in use.
PBS 1×:
450 ml aqua ad injectabila+50 ml 10×PBS
Stored at room temperature, storage life one year; two months in use.
NaHCO$_3$, 7.5%:
75 g NaHCO$_3$, Cat no. S-4019, Sigma
Dissolve in 1 l Millipore-H$_2$O.
Stored at 2-8° C., storage life one year; two months in use.
Hepes, 1M:
238.31 g Hepes, Cat no. S-4019, Sigma
33.75 ml NaOH 32%
Dissolve in 1 l Millipore-H$_2$O.
Stored at 2-8° C., storage life one year; four months in use.
L-glutamine, 0.2 M:
29.2 g L-glutamine, Cat no. G-5763, Sigma
Dissolve in 1 l Millipore-H$_2$O.
Stored at $\leq$−18° C. for one year; two months at 2-8° C. in use.

| Virus | Supplier of viruses used | Cell culture for virus propagation | Maintenance medium | Multiplicity of infection (MOI)[1] |
|---|---|---|---|---|
| Coxsackie A9 | Hygienisch-bakteriologisches Landesuntersuchungsamt "Westfalen" | HFF | MEM + 2% FCS | 0.005 |
| Adenovirus 3 | ATCC (ATCC NO: VR-847) | A549 | MEM + 2% FCS | 0.05 |
| Adenovirus 5 | ATCC (ATCC NO: VR-5) | A549 | MEM + 2% FCS | 0.05 |
| Human Cytomegalovirus (HCMV) strain AD-169 | ATCC (ATCC NO: VR-538) | HFF | MEM + 2% FCS | 0.02 |
| Human Cytomegalovirus (HCMV) Hi91 | own isolate9 | HFF | MEM + 2% FCS | 0.02 |
| Metapneumovirus | ATCC (ATCC NO: VR-92) | MK2 cells | MEM + 2 µg/ml trypsin | 0.1 |
| Echo virus 11 | own isolate | HFF | MEM + 2% FCS | 0.005 |
| Echo virus 30 | Hygienisch-bakteriologisches Landesuntersuchungsamt "Westfalen" | HFF | MEM + 2% FCS | 0.01 |
| Enterovirus 71 | own isolate | HFF | MEM + 2% FCS | 0.1 |

[1]The multiplicity of infection (MOI) is the ratio of infectious agents (e.g. phage or virus) to infection targets (e.g. cell).

Penicillin/Streptomycin:
10 MEGA Penicillin (penicillin), Grünenthal
10 g Streptomycin-Sulfate, Cat no. S-6501, Sigma
Dissolve in 1 l Millipore-$H_2O$.
Stored at $\leq -18°$ C. for one year; two weeks at 2-8° C. in use.

Trypsin/EDTA Solution:
2.0 g Trypsin 1:250 BAEE 1570 units/ml, Cat no. T-4799, Sigma
0.6 g EDTA-Na (Tritriplex III), Cat no. 8418.0100, Merck
Dissolve in 1 l 1×PBS.
Stored at $\leq -18°$ C. for one year; one month at 2-8° C. in use.

Serum-free MEM supplemented with 2% hepes, 2% $NaHCO_3$, 1% penicillin/streptomycin and containing 2 μg/ml trypsin was used as maintenance medium.

1.2 Determination of Antiviral Activity (Virus Yield Reduction Assay)

The virus yield reduction assay is a powerful technique for evaluating the efficacy of anti-viral compounds. This assay allows one to quantitate the production of infectious virions in drug-treated cultures in comparison to virus yields in untreated virus control. In this procedure virus-infected cultures are incubated with anti-viral compounds for a period sufficient to permit virus replication and then assayed for the presence of new progeny virus by titration on separate monolayer cultures (Shipman C Jr, Smith S H, Carlson R H, Drach J C (1976). Antiviral activity of arabinosyladenine and arabinosylhypoxanthine in herpes simplex virus-infected KB cells: selective inhibition of viral deoxyribonucleic acid synthesis in synchronized suspension cultures. Antimicrob Agents Chemother. 9: 120-127; Collins P, Bauer D J (1977). Relative potencies of anti-herpes compounds. Ann N Y Acad Sci. 284: 49-59; Prichard M N, Turk S R, Coleman L A, Engelhardt S L, Shipman C Jr, Drach J C (1990). A microtiter virus yield reduction assay for the evaluation of antiviral compounds against human cytomegalovirus and herpes simplex virus. J Virol Methods. 28: 101-106).

1.2.1 Assay Principle:

The assay was performed in cell culture flasks in triplicates. Two independent experiments were performed. Cells were counted and then infected after washing with PBS at a multiplicity of infection (MOI) as indicated at 4.1.1. FAV00A was simultaneously added (at the same time as virus) to the cell culture. The cells were incubated for 45 minutes at 37° C. to allow virus adsorption and then washed thrice with PBS to eliminate unadsorbed viruses. Afterwards, the set of infected cells that was pre-incubated with FAV00A was again treated with FAV00A. Virus control without addition of test or reference substance was also included in the assay. The culture flasks were incubated at 37° C. in a 5% $CO_2$-incubator. After 3 days (echo virus, enterovirus, coxsackievirus), 4 days (adenovirus), 5 days (cytomegalovirus), or 8 days (metapneumovirus) cells were frozen overnight and thawed the next day. The freezing and thawing steps allow the cells to disintegrate and release the virus they contain. In this way, the total amount of virus can be recovered. After a "low speed" centrifugation the viral amounts in each experimental setup (virus control as well as test or reference substance) is determined by performing an "end point titration" in 96-well plate—this gives the virus titre/amount at which 50% of cells are infected or uninfected ($TCID_{50}$/ml).

End Point Titration

One 96-well plate (for each experimental setup) with the susceptible cell culture was prepared according to SOP. Fifty μl of cell suspension was cultured in each well. Cells were cultured at 37° C. and in a 5% $CO_2$ atmosphere for three or four days to form a confluent monolayer. A 10-fold serial dilution (up to $10^{-9}$) of the recovered viruses following low speed centrifugation was made using the maintenance medium. On each plate, the $1^{st}$ and $2^{nd}$ rows (8 wells each) were used for cell culture control, $3^{rd}$-$12^{th}$ rows (8 wells each) were used for 10-fold serially diluted virus, beginning with undiluted virus stock and ending with the $10^{-9}$ diluted virus. Fifty μl from virus dilution was introduced into appropriate rows while 50 μl maintenance medium was added to the cell control rows. The plates were incubated for 2-3 days at 37° C. in a $CO_2$ incubator. After the incubation period, the plates were examined microscopically for cytopathogenic effect (CPE). The examination was performed independently, by two laboratory technicians. The virus titre was then calculated according to the method of Spearman and Kaerber (Spearman C (1908). The method of "right and wrong cases" ("constantstimuli") without Gauss's formulae. British Journal of Psychology 2: 227-242; Kärber G (1931). Beitrag zur kollektiven Behandlung pharmakologischer Reihenversuche [A contribution to the collective treatment of a pharmacological experimental series]. Archiv für experimentelle Pathologie and Pharmakologie 162: 480-483.). The % titre reduction in the test or reference substance in comparison to virus control (set to 100%) was then calculated.

1.3 Data Presentation

Virus yield reduction was expressed as $TCID_{50}$/ml and the % of virus infection as well as the fold reduction observed after treatment with test or reference substance relative to virus control (set to 100%) is indicated. As two independent experiments were conducted with the test and reference substances, mean values are presented in the tables shown below:

TABLE 13

Adenovirus 3

| | | FAV00A (μg/ml) | | |
|---|---|---|---|---|
| | Virus | 50 | 25 | 12.5 |
| | $6.1 \times 10^7 \pm$ $4.0 \times 10^6$ | $3.4 \times 10^7 \pm$ $2.5 \times 10^6$ (43.5%)[1] | $5.4 \times 10^7 \pm$ $1.6 \times 10^7$ (11.3%) | $7.2 \times 10^7 \pm$ $4.2 \times 10^7$ (n.a.[2]) |

TABLE 14

Adenovirus 5

| | | FAV00A (μg/ml) | | |
|---|---|---|---|---|
| | Virus | 50 | 25 | 12.5 |
| | $5.4 \times 10^8 \pm$ $1.6 \times 10^8$ | $1.7 \times 10^8 \pm$ $5.1 \times 10^7$ (68.4%)[1] | $3.0 \times 10^8 \pm$ $9.0 \times 10^7$ (43.7%) | $7.0 \times 10^8 \pm$ $3.9 \times 10^8$ (n.a.) |

TABLE 15

Human metapneumovirus

| | | FAV00A (μg/ml) | | |
|---|---|---|---|---|
| | Virus | 500 | 250 | 125 |
| | $4.5 \times 10^4 \pm$ $1.6 \times 10^4$ | $2.0 \times 10^3 \pm$ $1.6 \times 10^3$ (95.6%)[1] | $5.4 \times 10^4 \pm$ $1.6 \times 10^4$ (n.a.[2]) | $4.0 \times 10^4 \pm$ $2.2 \times 10^4$ (88.5%) |

TABLE 16

Enterovirus 71

| Virus | FAV00A (µg/ml) | | |
|---|---|---|---|
| | 200 | 100 | 50 |
| $4.0 \times 10^3 \pm$ $2.2 \times 10^3$ | $9.6 \times 10^1 \pm$ $2.8 \times 10^1$ $(97.6\%)[1]$ | $6.5 \times 10^2 \pm$ $4.6 \times 10^2$ $(83.6\%)$ | $5.4 \times 10^3 \pm$ $1.6 \times 10^3$ $(n.a.[2])$ |

TABLE 17

Coxsackie virus A9

| Virus | FAV00A (µg/ml) | | |
|---|---|---|---|
| | 50 | 25 | 12.5 |
| $3.1 \times 10^5 \pm$ $2.8 \times 10^5$ | $1.1 \times 10^5 \pm$ $7.9 \times 10^4$ $(65.3\%)[1]$ | $1.7 \times 10^5 \pm$ $5.2 \times 10^4$ $(45.7\%)$ | $1.7 \times 10^4 \pm$ $5.0 \times 10^4$ $(45.3\%)$ |

TABLE 18

Echo virus 11

| Virus | FAV00A (µg/ml) | | |
|---|---|---|---|
| | 250 | 125 | 62.5 |
| $3.0 \times 10^8 \pm$ $9.0 \times 10^7$ | $6.1 \times 10^7 \pm$ $4.4 \times 10^7$ $(79.9\%)[1]$ | $1.9 \times 10^8$ $(1.4 \times 10^8$ $(36.4\%)$ | $1.8 \times 10^8 \pm$ $1.6 \times 10^8$ $(41.8\%)$ |

TABLE 19

Echo virus 30

| Virus | FAV00A (µg/ml) | | |
|---|---|---|---|
| | 100 | 50 | 25 |
| $9.6 \times 10^7 \pm$ $2.8 \times 10^7$ | $3.0 \times 10^7 \pm$ $9.0 \times 10^6$ $(68.3\%)[1]$ | $7.9 \times 10^7 \pm$ $2.8 \times 10^7$ $(17.0\%)$ | $1.2 \times 10^8 \pm$ $8.2 \times 10^7$ $(n.a.[2])$ |

TABLE 20

Human cytomegalovirus Hi91

| Virus | FAV00A (µg/ml) | | |
|---|---|---|---|
| | 500 | 250 | 125 |
| $3.7 \times 10^4 \pm$ $1.2 \times 10^4$ | $2.4 \times 10^3 \pm$ $1.2 \times 10^3$ $(93.5\%)[1]$ | $5.2 \times 10^3$ $(3.5 \times 10^3)$ $(86.0\%)$ | $2.7 \times 10^4$ $(7.1 \times 10^3)$ $(24.9\%)$ |

TABLE 21

Human cytomegalovirus AD169

| Virus | FAV00A (µg/ml) | | |
|---|---|---|---|
| | 500 | 250 | 125 |
| $9.0 \times 10^4 \pm$ $3.0 \times 10^4$ | $5.3 \times 10^4 \pm$ $1.1 \times 10^4$ $(41.1\%)[1]$ | $1.0 \times 10^5 \pm$ $7.9 \times 10^4$ $(n.a.[2])$ | $2.2 \times 10^5 \pm$ $5.8 \times 10^4$ $(n.a.)$ |

2. Conclusion

The above data confirm that the test substance FAV00A shows antiviral activity against adenoviruses, coxsackievirus, echovirus, cytomegalovirus, metapneumovirus, and enterovirus as determined by virus yield assay.

In the experiments described above, the following abbreviations are used:
ATCC=American Type Culture Collection
BSA=bovine serum albumin
CPE=cytopathogenic effect
FCS=fetal calf serum
MDCK=Madin-Darby canine kidney
MEM=minimum essential medium eagle
MOI=multiplicity of infection
PBS=phosphate buffered saline
PCR=polymerase chain reaction
SDS=sodium dodecyl sulphate
SOP=standard operating procedure
$TC_{50}$=50% toxic concentration
$TCID_{50}$=50% tissue culture infective dose Impact of FAV00A on the Interferon Content in the Blood Plasma of Influenza Patients Significant elevation of IFN-α and IFN-γ levels versus the baseline values and Placebo group has been detected in volunteers exposed to FAV00A on the 7-th day of the drug intake (Visit V3). Increase of IFN-α levels was also observed in patients treated with Placebo, yet, this growth was less intensive than in FAV00A group (Table 22).

TABLE 22

Dynamics of circulating interferon levels of different types in blood serum of volunteers with acute respiratory infection from FAV00A/Placebo groups

| | | Parameter | | | | | | | |
|---|---|---|---|---|---|---|---|---|---|
| | | IFN-α | | | | IFN-γ | | | |
| Visit | Group | Mean value | P | Error of mean | Median | Mean value | P | Error of mean | Median |
| V1 | Placebo | 22.541 | 0.941 | 1.676 | 22.5 | 33.008 | 0.943 | 1.280 | 31.8 |
| | FAV00A | 22.290 | | 1.264 | 23.7 | 33.168 | | 0.912 | 33.25 |

TABLE 22-continued

Dynamics of circulating interferon levels of different types in blood serum of volunteers with acute respiratory infection from FAV00A/Placebo groups

| | | Parameter | | | | | | | |
|---|---|---|---|---|---|---|---|---|---|
| | | IFN-α | | | | IFN-γ | | | |
| Visit | Group | Mean value | P | Error of mean | Median | Mean value | P | Error of mean | Median |
| V3 | Placebo | 31.768* | <0.001 | 1.345 | 30.75* | 30.478* | <0.001 | 0.694 | 30.45* |
| | FAV00A | 37.563* | | 1.308 | 37.4* | 44.670* | | 0.765 | 45.85* |
| V4 | Placebo | 29.388* | 0.625 | 1.592 | 30.6* | 30.393* | <0.001 | 0.892 | 30.9* |
| | FAV00A | 30.072* | | 1.123 | 30.55* | 41.313* | | 0.770 | 40.1* |

P—confidence level of inter-group differences
*the differences in parameters are statistically significant versus V1 visit (detected by covariance analysis)

Circulating IFN-γ levels were decreased in the control group patients at third (V3) and fourth (V4) visits.

The results are indicative of interferonogenic effect of FAV00A. Increased IFN-α levels in the control group reflect induction of this protein as a response to viral infection.

It is well-known that viral infection activates different cell transcription systems, e.g. by production of several chemokines and cytokines. FAV00A intake makes its contribution into formation of body antiviral protection by stimulation of interferon I and immune interferon γ production. The latter one is predominantly produced by T-lymphocytes and activates monocytes. This process promotes polarization of T-cellular immune response in direction of type I T-helpers. As can be seen from the table, circulating IFN-γ levels were considerably increased in FAV00A-treated volunteers in 7 days after the therapy initiation, and remained high throughout reconvalescence period until 14-day of the study, which explains both therapeutic and preventive effects of the drug. IFN-γ levels were somewhat decreased in the control group during the study.

Thus, FAV00A intake has been shown to promote production of interferon types I and II determining its basic functions in cell-mediated protection from viral infections. The results of investigating FAV00A effect of body interferon status correlate with the data collected during statistical processing of volunteers' complete blood counts. Statistically significant (Wilcoxon test) decrease of blood monocytes level as percentage has been found to occur in the control group patients by the visits V3 and V4 (p=0.002 and p=0.033, respectively). No considerable decrease of blood monocytes level has been detected in patients treated with FAV00A throughout the study. This fact is indicative of limitation of viral infection immunosuppressive effect on cellular immunity responses in FAV00A treatment group.

The effect of the drug on cell-mediated immune responses improves clinical course of acute respiratory disease and limits possibilities of development of viral immunosuppression, complications, and transfer of infection into chronic one. Increase of IFN-γ production is of special importance, as, besides antiviral activity, it exerts various effects on immune system cells, myelomonocytic cells, and is deemed a key cytokine accompanying antigen stimulation of lymphocytes.

The invention claimed is:
1. α-Crystalline form of carbabenzpyride of formula (I):

$$\left[ \begin{array}{c} \text{O} \overset{\text{H}}{\underset{\text{N}}{\diagdown}} \text{C}_6\text{H}_5 \\ \text{pyridinium ring with } N^+\text{-CH}_3 \end{array} \right] \text{I}^-$$

exhibiting essentially the following powder X-ray diffraction data, measured using a diffractometer (copper anticathode) and expressed in terms of inter-planar distance d, Bragg's angle 2 theta, and relative intensity (expressed as a percentage with respect to the most intense ray) as shown in the table below listing the following reflex positions of high and medium intensity:

| No | Angle 2 theta (°) | Inter-planar distance d (Å) | Relative Intensity |
|---|---|---|---|
| 1 | 2.3925 | 36.92687 | 5.23 |
| 2 | 10.2105 | 8.66366 | 5.95 |
| 3 | 11.3179 | 7.81828 | 5.70 |
| 4 | 12.3706 | 7.15527 | 10.86 |
| 5 | 13.9617 | 6.34318 | 3.67 |
| 6 | 16.2837 | 5.44354 | 6.62 |
| 7 | 17.4171 | 5.09177 | 8.45 |
| 8 | 17.6238 | 5.03251 | 66.93 |
| 9 | 19.8858 | 4.46489 | 100.00 |
| 10 | 20.3088 | 4.37284 | 7.36. |

2. The α-crystalline form of carbabenzpyride according to claim 1 having a degree of purity of at least 99.5% as determined by HPLC.

3. The α-crystalline form of carbabenzpyride according to claim 2 having a degree of purity of at least 99.9% as determined by HPLC.

4. The α-crystalline form of carbabenzpyride according to claim 1 having a single endothermic maximum in its DSC curve in the range of 187 to 193° C.

5. The α-crystalline form of carbabenzpyride according to claim 1 having an IR-spectrum exhibiting the following characteristic peaks shown in the table below:

| Wave number [cm$^{-1}$] | vibration |
|---|---|
| 3236 | N—H |
| 3040 | C—H |
| 2934 | C—H |
| 1622 | C=O |
| 1600/1502 | C=C |
| 760/704 | C—H. |

6. A process for the preparation of the α-crystalline form of carbabenzpyride according to claim 1 comprising the following steps:
   (i) condensation of isonicotinic acid with benzylamine at elevated temperatures,
   (ii) crystallisation and isolation of the condensation product obtained in step (i) above,
   (iii) reaction of the crystalline product obtained in step (ii) above with methyl iodide and
   (iv) re-crystallisation of the crude product obtained in step (iii) from aqueous alcohol.

7. The process according to claim 6 wherein the condensation reaction between isonicotinic acid and benzylamine according to step (i) is carried out using an excess of benzylamine ranging from 10 to 25%.

8. The process according to claim 6 wherein the product of the condensation reaction between isonicotinic acid and benzylamide, benzylamide of isonicotinic acid (BAINA), is crystallised from the reaction mixture using a solvent selected from the group consisting of ethyl acetate, acetonitrile and isopropanol.

9. The process according to claim 8 further comprising the use of activated carbon.

10. The process according to claim 6 wherein the product of step (ii), BAINA, is treated with water.

11. The process according to claim 6 wherein in step (iii) the quaternisation reaction of benzylamide isonicotinic acid and methyl iodide is carried out using an excess of methyl iodide in the range of 5 to 15%.

12. The process according to claim 11 wherein the quaternisation reaction is carried out in an aqueous alcohol.

13. The process according to claim 12 wherein the aqueous alcohol is 90% ethanol.

14. The process according to claim 6 further comprising the step of washing the crude product obtained from step (iii) with an aqueous alcohol.

15. The process according to claim 14 wherein the aqueous alcohol is 96% ethanol.

16. The process according to claim 6 wherein the aqueous alcohol used in step (iv) is ethanol comprising water in an amount of 5 to 15% v/v.

17. The process according to claim 16 wherein the aqueous ethanol is 90% ethanol.

18. The process according to claim 6 wherein the ratio of the crude product and the aqueous alcohol used in step (v) is in the range of 1:2 to 1:4.

19. The process according to claim 18 wherein the ratio of the crude product and the aqueous alcohol used in step (v) is 1:3.

20. The process according to claim 6 wherein the re-crystallisation in step (iv) is carried out by spontaneously cooling the boiling aqueous ethanol solution of the crude product to a temperature in the range of 30 to 40° C. and further cooling the solution to a temperature in the range of 10 to 15° C. with further stirring over a period of time in the range of 1 to 3 hours.

21. A pharmaceutical composition comprising the α-crystalline form of carbabenzpyride of formula (I) according to claim 1 and a pharmaceutically acceptable carrier.

22. α-Crystalline form of carbabenzpyride of formula (I) according to claim 1 for use in the treatment and prevention of viral infections.

23. The α-crystalline form of carbabenzpyride according to claim 22 wherein the viral infections are infections caused by influenza (A) viruses.

24. The α-crystalline form of carbabenzpyride according to claim 23 wherein the viral infections are infections caused by A [H3N2 (California and Victoria/3/75), H1N1 (New Caledonia 20/99)].

25. The α-crystalline form of carbabenzpyride according to claim 22 wherein the viral infections are infections caused by adenoviruses, coxsackievirus, echovirus, cytomegalovirus, metapneumovirus, and enterovirus.

26. α-Crystalline form of carbabenzpyride of formula (I) according to claim 1 for use in the treatment of acute respiratory disease.

* * * * *